US00PP25138P3

(12) United States Plant Patent
Roberts

(10) Patent No.: US PP25,138 P3
(45) Date of Patent: Dec. 2, 2014

(54) MINT PLANT 'EVEREST MINT'

(50) Latin Name: ***Mentha* sp.**
Varietal Denomination: Everest Mint

(71) Applicant: Essex Laboratories, Inc., Napavine, WA (US)

(72) Inventor: Donald D. Roberts, Independence, OR (US)

(73) Assignee: Essex Laboratories, Inc., Napavine, WA (US)

( * ) Notice: Subject to any disclaimer, the term of this patent is extended or adjusted under 35 U.S.C. 154(b) by 0 days.

(21) Appl. No.: 13/986,043

(22) Filed: Mar. 25, 2013

(65) Prior Publication Data

US 2014/0289919 P1 Sep. 25, 2014

(51) Int. Cl.
*A01H 5/00* (2006.01)

(52) U.S. Cl.
USPC ..... Plt./259

(58) Field of Classification Search
USPC ..... Plt./259
See application file for complete search history.

(56) References Cited

U.S. PATENT DOCUMENTS

PP11,788 P2 2/2001 Roberts
PP13,720 P2 * 4/2003 Roberts ..... Plt./259

OTHER PUBLICATIONS

Gobert, V., "Hybridization in the section *Mentha* (Lamiaceae) inferred from AFLP markers," Am. J. Bot, Dec. 2002, 89 (12), pp. 2017-2023.
Fuchs, Sabine, et al., "Biosynthesis of Menthofuran in *Mentha×piperita*; Stereoselective and Mechanistic Studies"; J. Agric. Food Chem., 1999, 47 (10), pp. 4100-4105.
Dung, Jeremiah K.S., et al. Evaluation of *Verticillium* Wilt Resistance in *Mentha arvensis* and *M. longifolia* Genotypes, Plant Disease, Oct. 2010, vol. 94, pp. 1255-1260.
Verma, R.S., et al., Essential Oil Composition of Menthol Mint (*Mentha arvensis*) and Peppermint (*Mentha piperita*) Cultivars at Different Stages of Plant Growth from Kumaon Region of Western Himalaya; J. Medicinal and Aromatic Plants, India, 2010, vol. 1(1):pp. 13-18.

* cited by examiner

*Primary Examiner* — June Hwu
*Assistant Examiner* — Keith Robinson
(74) *Attorney, Agent, or Firm* — Marger Johnson & McCollom, PC

(57) ABSTRACT

Mint selection 11-A35-3, denominated 'Everest Mint', is a new *Mentha* sp. cultivar that produces an essential oil different in composition, produces a high oil yield, has an upright, bush type plant habit and has resistance to mint rust (*Puccinia menthae*) and mint wilt (*Verticillium dahlia*).

3 Drawing Sheets

Figure 1:
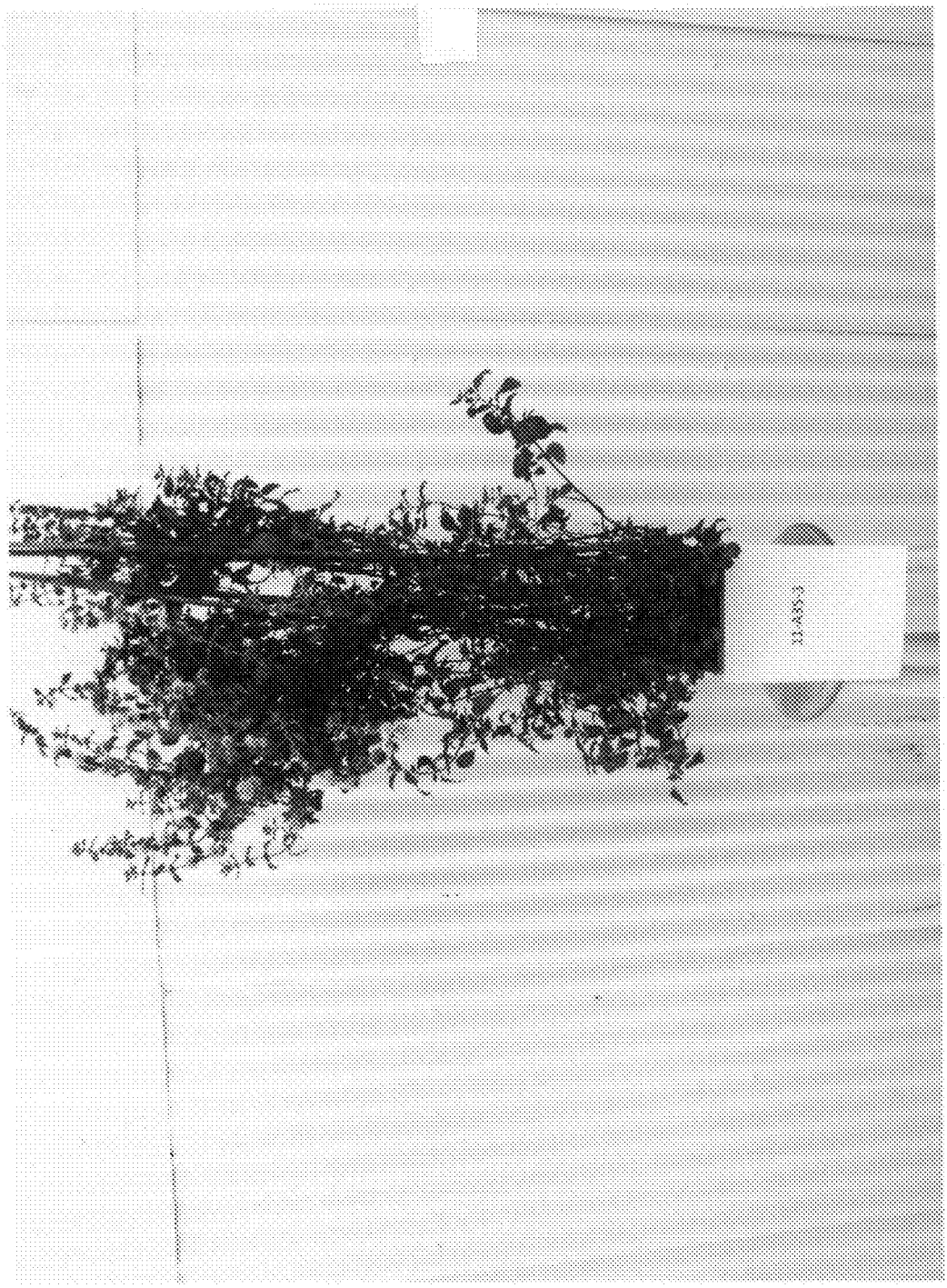

Latin name of the genus and species: *Mentha* sp.
Variety denomination: 'EVEREST MINT'.

FEDERAL SPONSORSHIP

None

TYPE OF PLANT AND NAME OF VARIETY

The present invention relates to a new and distinct variety of peppermint plant developed from a parent of the species *Mentha arvensis*. The new variety will be identified as 'Everest Mint'.

BACKGROUND OF THE INVENTION

This new mint was developed in a mint breeding program in which the primary objective was to develop a new peppermint variety having a specific oil composition, acceptable yield and resistant to mint diseases. The new variety is as resistant to mint wilt (soil borne fungus *Verticillium dahliae*) as its parent, but more resistant to mint rust (air-borne fungus *Puccinia menthae*). Selection 11-A35-3 has a higher yield of oil than the control variety, 'Black Mitcham', in test plots since 2011. This plant was selected from a population of mint seedlings in research plots on land near Monmouth, Oreg. and initially identified as 11-A35-3.

Selection 11-A35-3 originated as a seedling from an open pollinated *M. arvensis* female parent [09(Blanco×OP)]X OP included with male fertile *M. piperita* (polyploid 'Black Mitcham') plants in a polycross breeding program. Diploid *M. piperita* ('Black Mitcham') is sterile and only becomes fertile in the polyploidy state. The parent plants in the polycross breeding system were composed of selected fertile male and female genotypes based on certain desirable characteristics.

DISCOVERY AND ASEXUAL REPRODUCTION

Selection 11-A35-3 is asexually propagated by stem tip cuttings to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. Under the inventor's direction, Premier Botanicals has conducted asexual propagation of 11-A35-3 for greenhouse and field planting in Monmouth, Oreg., each year since 2011 and the genotype comes true to form with each generation.

SUMMARY OF THE INVENTION

Mint selection 11-A35-3, denominated 'Everest Mint', is a new *Mentha* sp. cultivar that produces an essential oil different in composition than commercially grown mint varieties. The essential oil is similar to standard mint oil in components composition but differs in the typical ratio of components. Organoleptically it differs from typical *M. piperita* 'Black Mitcham' peppermint oil. It is more resistant to mint rust than current commercially grown *M. arvensis* varieties.

BRIEF DESCRIPTION OF THE PHOTOGRAPHS

The accompanying color photographs show typical greenhouse and field grown vegetative growth of 11-A35-3 and depicts the color as nearly as reasonably possible.

Photograph 1 illustrates the growth habit under greenhouse conditions of my new mint plant.

Photograph 2 illustrates the type of flower, its color, and shape that develops on 11-A35-3.

Photograph 3 illustrates the type of leaf shape and the upright growth habit under field conditions of 11-A35-3.

DESCRIPTION OF PLANT

My new mint plant improves upon and is distinct from other mint plants in several characteristics, including but not limited to, the following:

1. The ability to produce an essential oil different in composition than typical commercial varieties of *M. arvensis*, but with similar components as 'Black Mitcham' peppermint (*M. piperita*);
2. Has a greater oil yield than currently grown mint varieties;
3. A more vigorous plant but with a branching pattern similar to its parent;
4. Has better resistance to common mint diseases than its parent and 'Black Mitcham' peppermint;

The essential oil extracted from 11-A35-3 has a composition of components more like that of oil produced by commercial *M. arvensis* than that of commercial *M. piperita*, as illustrated in Table 1. However, the ratio of oil components in 11-A35-3 is different from those of both commercial varieties of *M. arvensis* and *M. piperita*. The concentration of menthone in oil of 11-A35-3 is greater than that of commercial *M. arvensis* oil. There is only a trace of menthofuran present in the oil of 11-A35-3 and absent in oil of its parent and commercial *M. arvensis*. Menthyl acetate concentration is lower in the essential oil of 11-A35-3 than that in *M. piperita*, whereas, the menthol is higher in 11-A35-3 than *M. piperita*. Organoleptically, the oil of 11-A35-3 is different from that of 'Black Mitcham' and 'Shivalik', reflecting the difference in oil component ratios.

One of the primary selection pressures in the breeding program is for disease resistance, primarily for mint rust (*Puccinia menthae*) and mint wilt (*Verticillium dahliae*). No symptoms of either disease were observed in 11-A35-3 in multiple plant plots over a three year period. 'Blanco' and 'Black Mitcham' mint varieties served as control plants in the evaluation.

TABLE 1

A Comparison of 11-A35-3 Essential Oil collected from test plots near Monmouth, Oregon to that of its *M. arvensis* parent, Commercial *M. arvensis*, and Commercial *M. piperita* Oils.1/

| Essential Oil Components | [09(Blanco x OP)]X OP *Mentha arvensis* Parent seedling2/ | 11-A35-3 Seedling2/ | 'Shivalik' Commercial *M. arvensis* | 'Black Mitcham' Commercial *M. piperita* |
|---|---|---|---|---|
| 1-Limonene | 3.0 | 1.5 | 3.0 | 1.7 |
| 1,8-Cineole | <1.0 | <1.0 | <1.0 | 4.9 |
| 1-Menthone | 15.7 | 19.9 | 7.3 | 19.4 |
| Menthofuran | 0.0 | <1.0 | 0.0 | 4.2 |
| Isomenthone | 3.5 | 4.5 | 3.6 | 3.1 |
| 1-Menthyl Acetate | 3.7 | 2.1 | 2.9 | 5.3 |
| 1-Menthol | 64.3 | 62.6 | 73.9 | 44.6 |
| Pulegone | <1.0 | <1.0 | 0.0 | 2.1 |

The numbers listed in the above table are percentages based upon the analysis of the respective mint oils by gas chromatography. The percentages are determined by calculation of the relative peak areas.
1/Commercial essential oils of *M. arvensis* and *M. piperita* were what is typically produced by mint growers.
2/The essential oil of *M. arvensis* parent seedling [09(Blanco x OP)] X OP and 11-A35-3 were collected from plants growing in test plots in 2012.

TAXONOMIC DESCRIPTION OF 11-A35-3

This new plant, under greenhouse and field growing conditions, is an upright, bush type plant (Photograph 3) with lateral branches at each node of the main stem. It spreads from underground stolons. The height of 11-A35-3 is greater than 'Black Mitcham' growing under similar conditions and will vary based on fertilizer, soil quality, water application, amongst other known factors that affect growth patterns. The height of 11-A35-3 under field conditions and at the flowering stage is 0.76 to 1 m, (Photograph 3). The height of 11-A35-3 grown as a single plant is between 0.75 to 1.3 m and has a width of 0.3 to 0.45 m, (Photograph 1). Secondary and tertiary branching occurs to form a compact upright growth habit. The main stem at mid-plant (approximately between the eleventh and twelfth node) of a mature plant is 4.2-5.2 mm in width. The secondary and tertiary branch stems are 2.0-3.4 mm and 1-2 mm in width, respectively.

Mature leaves at the bottom of the plant are ovate lanceolate as are leaves on secondary branch stems. Leaves on upper mature plants, both main and secondary stems are more lanceolate (Photographs 1 and 3). Leaf surface is sub-glabrose on upper surface with very small hairs uniformly covering the surface. Small hairs are present on vein ridges on the underside of the leaf. Oil glands are distributed across the underside of the leaf. Fragrance of the leaf is a strong peppermint with a menthol note. Mid-main stem leaf size at flowering is 30-34 mm in width and 55-65 mm in length. Leaf size on secondary branches at flowering is 18-24 mm in width and 35-40 mm in length. Leaf petioles on the main stem leaves are 10-13 mm in length while petioles on secondary branch stem leaves are 4-7 mm in length. Leaves on the mid-main and lower stem tend to be less dentate than 'Black Mitcham' peppermint leaves while the leaves on the upper plant tend to be more dentate and similar to 'Black Mitcham' peppermint leaves. The main stem leaves have from 8-11 teeth on each side while the secondary branch leaves have 7-11 teeth on each side. The leaf is green in color, ranging from Fifth Edition Royal Horticultural Society Colour Chart N137C to N137D in the Fan 3 green group classification. The leaf has 6-9 lateral veins, more or less in parallel off the main vein that runs from the petiole to the tip of the leaf. The veins are prominent in all leaves of 11-A35-3. Seed produced by 11-A35-3 varies in color from brown (Fifth Edition Royal Horticultural Society Colour Chart 177A, Fan 4 Greyed-Orange Group) to black (Fifth Edition Royal Horticultural Society Colour Chart 203B, Fan 4 Black Group), oval in shape with a width of 0.4 to 0.6 mm and a length of 0.6 to 0.8 mm.

The inflorescence is a conspicuous spike with capitate flowers developing at the nodes of the spike stem. The cylindrical spikes are about 30 mm in diameter and indeterminate in growth. The capitate flowers are 15-20 mm in width and 10-15 mm in length. The flowers consist of five petals fused into a two lipped corolla. The corolla is white light violet in color as illustrated in The Fifth Edition Royal Horticultural Society Colour Chart 91D in the Fan 2 Violet-Blue Group. The calyx is generally yellow green and is 142A to 142B RHS, Fan 3 Green Group as illustrated in The Fifth Edition Royal Horticultural Colour Chart index. The gynoecium consists of a single pistil with two lobed stigma that is exserted. The androecium consists of four stamens, each with a distinct filament and anther.

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of mint plant, substantially as shown and described, characterized particularly by improved vigor and producing a unique essential oil.

* * * * *

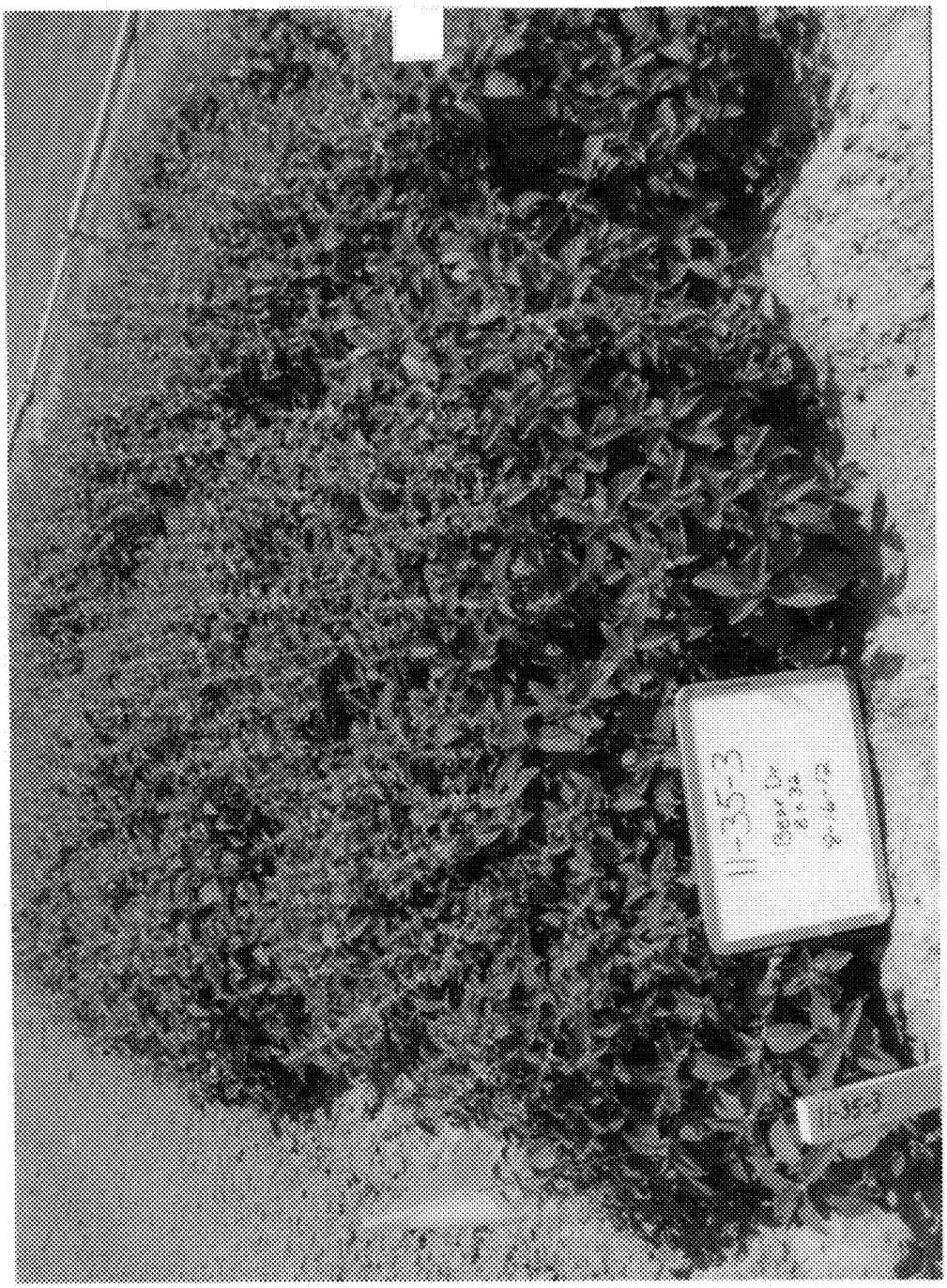

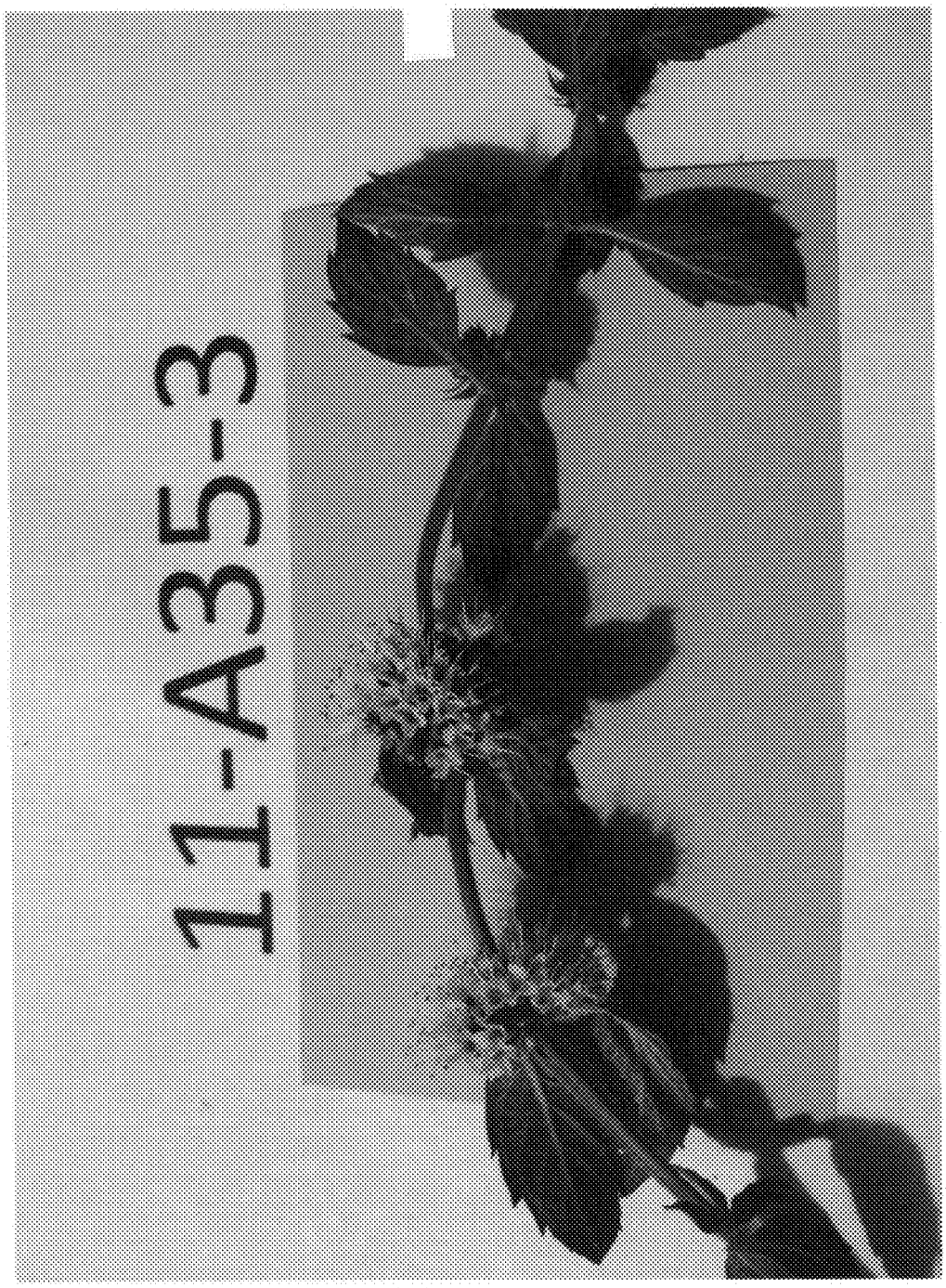
11-A35-3